US008697907B2

(12) United States Patent
Key et al.

(10) Patent No.: US 8,697,907 B2
(45) Date of Patent: Apr. 15, 2014

(54) PROCESS FOR THE PRODUCTION OF ACETIC ACID

(75) Inventors: Lesley Ann Key, Hull (GB); Andrew David Poole, Brough (GB)

(73) Assignee: BP Chemicals Limited, Middlesex (GB)

( * ) Notice: Subject to any disclaimer, the term of this patent is extended or adjusted under 35 U.S.C. 154(b) by 960 days.

(21) Appl. No.: 12/225,244

(22) PCT Filed: Mar. 16, 2007

(86) PCT No.: PCT/GB2007/000954
§ 371 (c)(1),
(2), (4) Date: Sep. 17, 2008

(87) PCT Pub. No.: WO2007/107724
PCT Pub. Date: Sep. 27, 2007

(65) Prior Publication Data
US 2010/0228051 A1    Sep. 9, 2010

(30) Foreign Application Priority Data
Mar. 21, 2006 (EP) .................................. 06251506

(51) Int. Cl.
*C07C 51/12*    (2006.01)
(52) U.S. Cl.
USPC ........................................................ 562/519
(58) Field of Classification Search
None
See application file for complete search history.

(56) References Cited

U.S. PATENT DOCUMENTS

| | | | |
|---|---|---|---|
| 6,103,934 A | 8/2000 | Hallinan et al. | |
| 6,140,535 A | 10/2000 | Williams | |
| 6,362,366 B1 | 3/2002 | Hallinan et al. | |
| 6,552,221 B1 | 4/2003 | Hallinan et al. | |
| 2005/0131251 A1 | 6/2005 | Law | |
| 2005/0165251 A1* | 7/2005 | Muskett | 562/519 |
| 2005/0176996 A1* | 8/2005 | Law et al. | 562/550 |

FOREIGN PATENT DOCUMENTS

| | | |
|---|---|---|
| EP | 0 161 874 | 11/1985 |
| EP | 0 643 034 | 3/1995 |
| EP | 0 728 726 | 8/1996 |
| EP | 0 728 727 | 8/1996 |
| EP | 0 849 248 | 6/1998 |
| EP | 0 849 250 A1 | 6/1998 |
| JP | 58-151327 | 8/1983 |
| JP | H10-273470 | 10/1998 |
| WO | 00/24701 | 5/2000 |
| WO | 02/04394 | 1/2002 |
| WO | 03/097567 | 11/2003 |
| WO | 03/106396 | 12/2003 |

OTHER PUBLICATIONS

Fujihara et al. (Dalton Trans., 2004, 645).*
Omberg et al. (J. Am. Chem. Soc., 1997, 119, 7013).*
International Search Report for PCT/GB2007/000954 mailed Jun. 27, 2007.
Written Opinion for PCT/GB2007/000954 mailed Jun. 27, 2007.
English translation of Office Action issued in corresponding Japanese Patent Application No. 2009-500913, date of draft Jul. 9, 2012 (4 pgs).

* cited by examiner

*Primary Examiner* — Johann R Richter
*Assistant Examiner* — Jennifer C Sawyer
(74) *Attorney, Agent, or Firm* — Nixon & Vanderhye P.C.

(57) ABSTRACT

Process for producing acetic acid by carbonylating methanol and/or a reactive derivative thereof in a liquid reaction composition in which there exists in equilibrium, at least a first soluble catalytic species and a second soluble catalytic species. The first catalytic species is the least catalytically active or promotionally active of the species existing in the equilibrium. The process includes determining (i) the concentration of the first catalytic species and/or (ii) the ratio of the concentration of the first catalytic species to the concentration of the second catalytic species in equilibrium therewith, present in the liquid reaction composition and/or a present in a liquid fraction in a separation step, and maintaining (i) and/or (ii) below a pre-determined value.

10 Claims, 1 Drawing Sheet

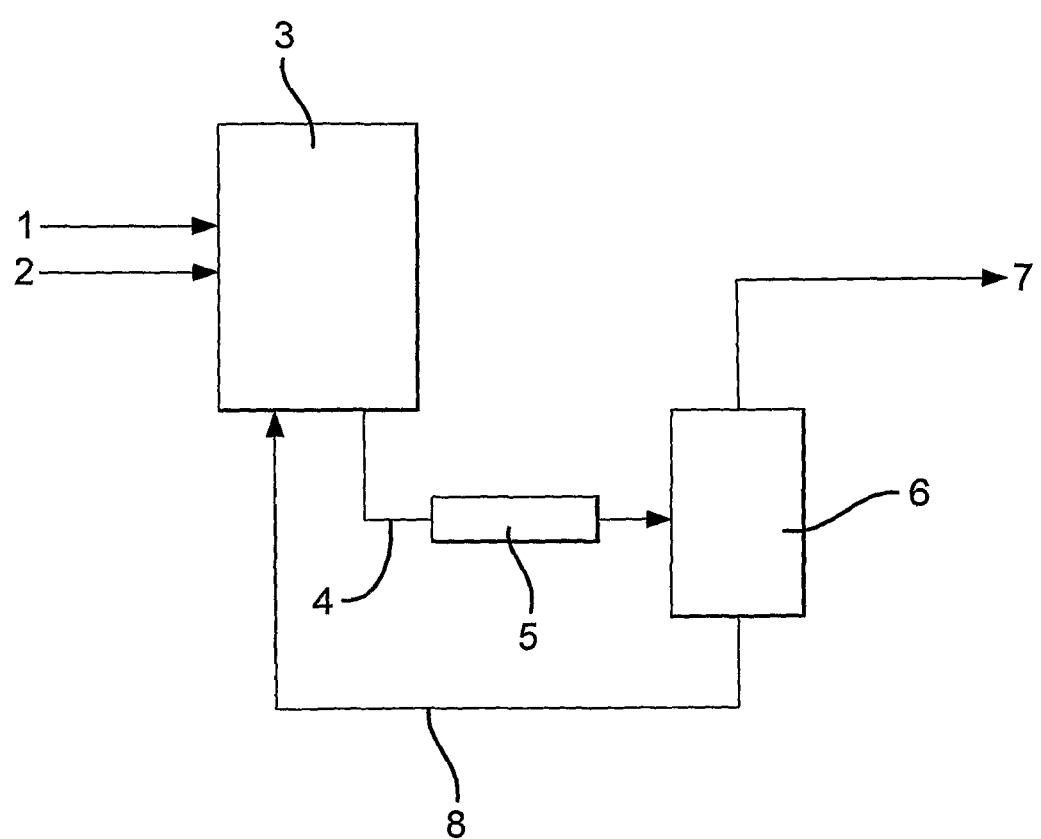

PROCESS FOR THE PRODUCTION OF ACETIC ACID

The present invention relates to a process for the production of acetic acid by carbonylation of methanol and/or a reactive derivative thereof in the presence of a catalyst and a catalyst promoter metal.

BACKGROUND OF THE INVENTION

The production of acetic acid by carbonylation of methanol and/or a reactive derivative thereof is a known process, having been reviewed, for example, by Howard et al in Catalysis Today, 1993, 18, 325-254. Typical catalysts employed in homogeneously catalysed carbonylation processes are rhodium, iridium, or a combination of rhodium and iridium as described, for example, in EP-A-0 161 874, EP-A-0 849 248 and EP-A-1 123 265 respectively. Such catalyst metals are often used in combination with one or more promoter metals, such as rhenium (EP-A-0 728 726), or ruthenium and/or osmium (EP-A-0 643 034 & EP-A-0 728 727).

It is known that catalysts and catalyst promoter metals are typically present in methanol carbonylation processes as a mixture of catalytic species, some of which species are less catalytically or promotionally active than other species, for example, as described in D. Forster, J. Chem. Soc., Dalton Trans., 1979, 1639. It is further known that under certain circumstances the less active species can be more prone to precipitation. For example, U.S. Pat. No. 6,103,934 describes a rhodium catalysed methanol carbonylation process in which rhodium is present as a mixture of the active form $Rh(CO)_2I_2^-$ and the inactive form $Rh(CO)_2I_4^-$, the inactive form being more prone to precipitation than the active form.

WO 03/106396 describes how the use of low concentrations of specified iodides can reduce precipitation in iridium-catalysed carbonylation processes. Further, WO 03/097567 describes how precipitation in a ruthenium-promoted iridium catalysed carbonylation process can be reduced by maintaining a defined amount of carbon monoxide in the acetic acid recovery stage of the process. However, the amount of iodide added to the process described in WO 03/106396 is dependent on the total amount of iridium catalyst present in the carbonylation process; and the defined amount of carbon monoxide maintained in the process described in WO 03/097567 is dependent on the total amount of ruthenium promoter present in the process. Neither WO 03/106396 nor WO 03/097567 describes the specific iridium or ruthenium species which can result in the formation of precipitates in the carbonylation process. Thus, the processes of WO 03/106396 and WO 03/097567 may result in more iodide, or more carbon monoxide being employed than is actually required to reduce precipitates, i.e. resources may be wasted.

Infrared spectroscopy has hitherto been applied to carbonylation processes, for example, in analysing the concentrations of components of a liquid reaction composition, and adjusting the concentrations in response thereto, as described in U.S. Pat. No. 6,552,221 and U.S. Pat. No. 6,103,934. However, U.S. Pat. No. 6,552,221 makes no mention of employing infrared to measure the concentrations of catalytic species present in the liquid reaction composition; and U.S. Pat. No. 6,103,934 requires that the concentrations of a variety of components of the reaction composition are determined, in particular, the concentrations of at least methyl iodide, water and the active catalytic species present in the reaction composition must be determined.

SUMMARY OF THE INVENTION

Thus, there remains a need for an optimised process for the production of acetic acid by carbonylation of methanol and/or reactive derivative thereof.

Accordingly the present invention provides a process for the production of acetic acid which process comprises the steps of:

(a) carbonylating methanol and/or a reactive derivative thereof with carbon monoxide in a first reaction zone containing a liquid reaction composition comprising a carbonylation catalyst and a carbonylation catalyst promoter metal, methyl iodide, methyl acetate, acetic acid and optionally water, and in which liquid reaction composition there exists in equilibrium at least a first soluble catalytic species and a second soluble catalytic species, wherein the first catalytic species is the least catalytically active or promotionally active of the species existing in the equilibrium;

(b) withdrawing liquid reaction composition together with dissolved and/or entrained carbon monoxide and other gases from said first reaction zone;

(c) optionally passing said withdrawn liquid reaction composition through one or more further reaction zones to consume at least a portion of the dissolved and/or entrained carbon monoxide;

(d) passing said liquid reaction composition from step (b) and optional step (c) into one or more flash separation stages to form a vapour fraction, which comprises condensable components and low-pressure off-gas, the condensable components comprising acetic acid product, methyl iodide, methyl acetate and optional water, and the low-pressure off-gas comprising carbon monoxide and other gases dissolved and/or entrained in the withdrawn liquid reaction composition, and a liquid fraction, which comprises carbonylation catalyst, carbonylation catalyst promoter metal and acetic acid solvent; and (e) recycling the liquid fraction from the flash separation stage to the first reaction zone;

(f) determining (i) the concentration of the first catalytic species and/or (ii) the ratio of the concentration of the first catalytic species to the concentration of the second catalytic species in equilibrium therewith, present in the liquid reaction composition in any of steps (a) to (d), and/or present in the liquid fraction in step (e); and (g) maintaining (i) and/or (ii) below a pre-determined value, preferably by adjusting the concentration of at least the first catalytic species present in the liquid reaction composition in any of steps (a) to (d), and/or present in the liquid fraction in step (e).

The first and second catalytic species are either different forms of the catalyst or different forms of the catalyst promoter metal. Preferably, the first and second soluble catalytic species are different forms of the catalyst promoter metal Since the first catalytic species is less catalytically or promotionally active than at least the second catalytic species, the concentration of the first catalytic species or the ratio of the concentrations of the first and second catalytic species in the liquid reaction composition or the liquid fraction may affect one or more reaction parameters, such as reaction rate, selectivity towards desired product or products and/or catalyst stability or lifetime.

Thus, the present invention allows optimisation of a process for the production of acetic acid by carbonylation of methanol and/or reactive derivative thereof by allowing the concentration of the first catalytic species and/or the ratio of the concentrations of the first and second catalytic species to be maintained below a value at which one or more of the reaction rate, selectivity or catalyst stability or lifetime would be adversely affected. Advantageously, in the process of the present invention, the concentration of the first catalytic species need only be adjusted to the extent that is necessary to maintain the concentration of the first soluble catalytic species, and/or concentration ratio of the first to second soluble catalytic species to below the predetermined value, thereby avoiding any waste of resources. Further, the present invention requires only a determination of the concentration of the first catalytic species and/or the ratio of the concentrations of the first and second catalytic species in the liquid reaction composition or the liquid fraction, it is unnecessary to determine the concentrations of other catalytic species or of further components present in the liquid reaction composition or the liquid fraction.

In the process of the present invention, there may be several soluble catalytic species present in the liquid reaction composition, which are in equilibrium with each other, and which each have different catalytic or promotional activity. Thus, in addition to being in equilibrium with a second soluble catalytic species having a higher catalytic or promotional activity, the first soluble catalytic species may also be in equilibrium with further soluble catalytic species of higher catalytic or promotional activity.

The process of the present invention may employ a transition metal catalyst in the presence of a second transition metal which acts as the catalyst promoter. In such a case, both the transition metal catalyst and transition metal promoter will each exist as more than one soluble catalytic species in the liquid reaction composition and the liquid fraction. In particular, a number of soluble transition metal carbonyl complexes will exist in equilibrium with each other. Thus, in the process of the present invention the first and second soluble species may therefore be carbonyl complexes of a transition metal catalyst, or carbonyl complexes of a transition metal promoter.

Preferably the catalyst comprises rhodium, iridium or mixtures thereof. Where the catalyst is iridium, the catalyst promoter metal may be selected from the group consisting of ruthenium, osmium, rhenium, cadmium, mercury, zinc, gallium, indium, tungsten and mixtures thereof. Where the catalyst is rhodium, the promoter metal may be selected from the group consisting of ruthenium, osmium, rhenium, manganese and mixtures thereof.

Thus, in this embodiment, the first soluble catalytic species could be a soluble rhodium or iridium catalytic species which is in equilibrium with at least a second soluble rhodium/iridium catalytic species, the second species having a higher catalytic activity than the first. For example, where rhodium is employed as the catalyst, the first soluble catalytic species may be $[Rh(CO_2)I_4]^-$ and the second soluble catalytic species may be $[Rh(CO)_2I_2]^-$. Where iridium is employed as the catalyst, the first catalytic species may be $[Ir(CO)_2I_4]^-$ and the second catalytic species may be $[Ir(CO)_2I_3CH_3]^-$. Alternatively, the first soluble catalytic species could be a soluble promoter metal catalytic species which is in equilibrium with at least a second soluble promoter metal catalytic species, the second species having a higher promotional activity than the first. For example, where the catalyst is iridium and the catalyst promoter metal is ruthenium a number of soluble ruthenium species exists in the liquid reaction composition and the liquid fraction, such as $[Ru(CO)_3I_3]^-$, $[Ru(CO)_4I_2]$ and $[Ru(CO)_2I_2]_n$, which exist in equilibrium with each other.

The concentration of the first catalytic species or the ratio of the concentration of the first catalytic species to at least the concentration of the second catalytic species may be determined by infrared spectroscopy, for example, mid-infrared spectroscopy. Infrared spectroscopy is advantageous, since it is non-destructive, can be carried out either on-line or off-line, and allows both qualitative and quantitative information on the composition of the liquid reaction composition or of the liquid fraction to be obtained.

The concentrations of the soluble catalytic species may be determined, for example, by comparing an infrared spectrum of the liquid reaction composition or the liquid fraction with the infrared spectra of a series of solutions comprising the first soluble catalytic species in known concentrations or the first and second soluble catalytic species in known concentration ratios. In one embodiment of the invention, the concentration ratio of the first to the second soluble catalytic species may be determined in this manner on the basis of one or more specific portions of an infrared spectrum where the first and second soluble catalytic species have preferred absorption characteristics, for example, a specific infrared band or frequency for each of the first and second soluble catalytic species.

The separate concentrations and/or the concentration ratio of the first and second soluble catalyst metal species can be determined from the infrared spectrum as a whole or in part, for example from all or part of the mid-infrared range of 4000 to 400 $cm^{-1}$. For example, where the first and second soluble catalyst species comprise metal carbonyl complexes, a suitable range would be from 2500 to 1500 $cm^{-1}$. Alternatively, individual frequencies or separate ranges of frequencies relating to specific absorbance bands of the soluble catalytic species can be used.

Since the first and second catalytic species may be either different forms of the catalyst or different forms of the catalyst promoter metal, it may be advantageous to determine the concentration and/or concentration ratios of species present in the liquid reaction composition or the liquid fraction for which more accurate concentration and/or concentration ratios can be obtained, for example, by determining the concentration or ratio of concentrations of species which exhibit stronger or sharper infrared absorption bands. For example, in iridium-catalysed, ruthenium-promoted carbonylation of methanol, infrared-active absorbances of ruthenium-carbonyl species tend to have higher extinction coefficients, and hence tend to show stronger absorption bands, than iridium species, allowing more accurate determination of the concentration or concentration ratio of ruthenium species.

According to the present invention, the concentration of the first soluble catalytic species and/or the concentration ratio of the first to the second soluble catalytic species present in the liquid reaction composition of any of steps (a) to (d), or present in the liquid fraction in step (e) is determined. Preferably, the concentration ratio of the first to the second soluble catalytic species present in the liquid fraction in step (e) is determined.

In response to the determined concentration of the first soluble catalytic species or concentration ratio of the first to the second soluble catalytic species present in the liquid reaction composition and/or the liquid fraction, the concentration of the first soluble catalytic species may be adjusted in order to maintain the concentration of the first soluble catalytic species, or concentration ratio of the first to second soluble catalytic species below a predetermined value. The concentration may be adjusted directly, for example, by adjusting the composition of the liquid reaction composition, or may be adjusted indirectly, for example, by adjusting conditions in the first and optional further reaction zones, such as temperature or pressure.

For example, conditions in the first reaction zone and or optional further reaction zones may be adjusted to shift the equilibrium in favour of the second species, which has higher catalytic or promotional activity, thereby adjusting the concentration of the first soluble catalytic species in the liquid reaction composition or liquid fraction such that said concentration or the ratio of the concentrations of the first and second soluble catalytic species may be maintained below a predetermined value. In a methanol carbonylation process according to the present invention, this can be achieved, for example, by adjusting the partial pressure of carbon monoxide in the first reaction zone, which results in a corresponding adjustment of the concentration of carbon monoxide dissolved in the liquid reaction composition, by adjusting the temperature or pressure in the first reaction zone, or by adjusting the concentration of one or more components of the liquid reaction composition, such as methanol.

In a preferred embodiment of the present invention the catalyst is iridium, the catalyst promoter metal is ruthenium and the process relates to reducing the precipitation of ruthenium. In such an embodiment, soluble $[Ru(CO)_3I_3]^-$, $[Ru(CO)_4I_2]$ and $[Ru(CO)_2I_2]_n$ species exist in equilibrium in the liquid reaction composition and the liquid fraction. The species $[Ru(CO)_2I_2]_n$ can precipitate from the liquid reaction composition or the liquid fraction when "n" is greater than 1, resulting in loss of ruthenium from the process. Thus, in this embodiment, the first soluble catalytic species is $[Ru(CO)_2I_2]_n$. The second soluble catalytic species may be $[Ru(CO)_4I_2]$ or $[Ru(CO)_3I_3]^-$ both of which are more promotionally active than $[Ru(CO)_2I_2]_n$. $[Ru(CO)_3I_3]^-$, $[Ru(CO)_4I_2]$ and $[Ru(CO)_2I_2]_n$ are each detectable by mid-infrared spectroscopy, in particular, bands at 2107 and 2037 $cm^{-1}$ are observed for $[Ru(CO)_3I_3]^-$, at 2165, 2107, 2075 and 2020 $cm^{-1}$ for $[Ru(CO)_4I_2]$, and at 2054 and 1992 $cm^{-1}$ for $[Ru(CO)_2I_2]_n$. Thus, precipitation of ruthenium in the process can be reduced or prevented by determining either the concentration of $[Ru(CO)_2I_2]_n$ or the ratio of the concentrations of $[Ru(CO)_2I_2]_n$ and one of $[Ru(CO)_3I_3]^-$ or $[Ru(CO)_4I_2]$, using mid-infrared spectroscopy, and adjusting the concentration of the first catalytic species such that the concentration or the ratio of concentrations is maintained below a value at which precipitation would occur. Preferably, the ratio of the concentration of $[Ru(CO)_2I_2]_n$ to the concentration of $[Ru(CO)_3I_3]^-$ is determined and adjustment of the concentration of $[Ru(CO)_2I_2]_n$ is carried out by adjustment of the feed rate of carbon monoxide to the first, and/or optional further reaction zones.

Suitable iridium and ruthenium compounds that may be added to the liquid reaction composition, and which are capable of converting to catalytically and promotionally active species, are described in EP-A-0 144 935, EP-A-0 643 034 and U.S. Pat. No. 6,211,405.

Examples of suitable iridium compounds include iridium (III) chloride, iridium(III) bromide, iridium(III) iodide, $IrCl_3.4H_2O$, $IrBr_3.4H_2O$, $[Ir(CO)_2Cl]_2$, $[Ir(CO)_2Br]_2$, $[Ir(CO)_2I]_2$, $H[Ir(CO)_2Cl_2]$, $H[Ir(CO)_2Br_2]$, $H[Ir(CO)_2I_2]$, $H[Ir(CH_3)I_3(CO)_2]$, $Ir_3(CO)_{12}$, $Ir_4(CO)_{12}$, iridium metal, $Ir_2O_3$, $IrO_2$, $Ir(acetylacetonate)(CO)_2$, $Ir(acetylacetonate)_3$, iridium acetate, and $H_2[IrCl_6]$. Preferably the complexes are chloride-free, such as acetates, oxalates and acetylacetonates. Preferably the iridium is present in the liquid reaction composition for the carbonylation reaction in the range 100 to 6000 ppm by weight of iridium, preferably from 400 to 3000 ppm.

Examples of suitable ruthenium-containing compounds include ruthenium(III) chloride, ruthenium(III) chloride trihydrate, ruthenium(III) bromide, ruthenium(III) iodide, ruthenium(IV) chloride, ruthenium metal, ruthenium oxides, ruthenium(III) formate, $H[Ru(CO)_3I_3]$, tetra(aceto)chlororuthenium(II,III), ruthenium(III)acetate, ruthenium(III) propionate, ruthenium(III) butyrate, ruthenium pentacarbonyl, triruthemiumdodecacarbonyl and mixed ruthenium halocarbonyls such as dichlorotricarbonylruthenium(II) dimer, dibromotricarbonylruthenium(II) dimer, and other organoruthenium complexes such as tetruchlorobis(4-cymene)diruthenium(II), tetrachlorobis(benzene)diruthenium(II), dichloro(cyclooctadiene)ruthenium(II) polymer and tris(acetylacetonate)ruthenium(III). Suitably the molar ratio of ruthenium:iridium is in the range of from 0.5:1 to 15:1

The first reaction zone may comprise a conventional liquid-phase carbonylation reaction zone. The pressure of the carbonylation reaction in the first reaction zone is suitably in the range 17 to 100 bara (1.7 to 10.0 MPa), preferably 20 to 80 bara (2.0 to 8.0 MPa), more preferably 20 to 40 bara (2.0 to 4.0 MPa). The temperature of the carbonylation reaction in the first reaction zone is suitably in the range 100 to 300° C., preferably in the range 170 to 220° C.

In iridium-catalysed processes, it is preferred that at least two reaction zones are employed, the first and second reaction zones being maintained in separate reaction vessels with means for withdrawing from the first reaction vessel and passing to the second reaction vessel liquid reaction composition from the first reaction vessel with dissolved and/or entrained carbon monoxide. Such a separate second reaction vessel may comprise a section of pipe between the first reaction vessel and a liquid reaction composition flashing valve. Preferably the pipe is liquid full. Typically the pipe's length to diameter ratio may be about 12:1, though length to diameter ratios both higher and lower than this may be employed.

Typically, at least a portion of the liquid reaction composition together with dissolved and/or entrained carbon monoxide is withdrawn from the first reaction zone and at least a portion of the withdrawn liquid and dissolved and/or entrained carbon monoxide passed to the second reaction zone. Preferably substantially all the liquid reaction composition together with dissolved and/or entrained carbon monoxide withdrawn from the first reaction zone is passed to the second reaction zone.

The second reaction zone may be operated at a reaction temperature in the range 100 to 300° C., preferably in the range 150 to 230° C. The second reaction zone may be operated at a temperature higher than the first reaction zone, typically up to 20° C. higher. The second reaction zone may be operated at a reaction pressure in the range 10 to 200 barg, preferably in the range 15 to 100 barg. Preferably, the reaction pressure in the second reaction zone is equal to or less than the reaction pressure in the first reaction zone. The residence time of liquid reaction composition in the second reaction zone is suitably in the range 5 to 300 seconds, preferably 10 to 100 seconds.

There may be introduced to the second reaction zone carbon monoxide in addition to that introduced to the second reaction zone as dissolved and/or entrained carbon monoxide. Such additional carbon monoxide may be co-joined with the first liquid reaction composition prior to introduction to the second reaction zone and/or may be fed separately to one or more locations within the second reaction zone. Such additional carbon monoxide may contain impurities, such as for example hydrogen, nitrogen, carbon dioxide and methane. The additional carbon monoxide may be comprised of high pressure off-gas from the first reaction zone which could advantageously allow the first reaction zone to be operated at a higher CO pressure with the resulting higher flow of carbon monoxide being fed to the second reaction zone. Additionally it could eliminate the requirement for a high pressure off-gas treatment.

The additional carbon monoxide may also be comprised of another carbon monoxide-containing gas stream such as for example a carbon monoxide-rich stream from another plant.

Preferably greater than 10%, more preferably greater than 25%, even more preferably greater than 50%, for example at least 95%, of the dissolved and/or entrained carbon monoxide in the withdrawn reaction composition from the first reaction zone is consumed in the second reaction zone.

In the process of the present invention, suitable reactive derivatives of methanol include methyl acetate, dimethyl ether and methyl iodide. A mixture of methanol and reactive derivatives thereof may be used as reactants in the process of the present invention. Preferably, methanol and/or methyl acetate are used as reactants.

At least some of the methanol and/or reactive derivative thereof will be converted to, and hence present as, methyl acetate in the liquid reaction composition by reaction with the carboxylic acid product or solvent. Preferably, the concentrations of methyl acetate in the liquid reaction compositions in the first and optional further reaction zones are independently in the range 0.25 to 70% by weight, more preferably 0.5 to 50% by weight.

Water may be formed in situ in the liquid reaction compositions, for example, by the esterification reaction between methanol reactant and acetic acid product. Water may be introduced independently to the first and second carbonylation reaction zones together with or separately from other components of the liquid reaction compositions. Water may be separated from other components of reaction compositions withdrawn from the reaction zones and may be recycled in controlled amounts to maintain the required concentration of water in the liquid reaction compositions. For iridium catalysed methanol carbonylation, the concentrations of water in the liquid reaction compositions in the first and optional further reaction zones are preferably independently in the range 0.1 to 10% by weight. For rhodium catalysed methanol carbonylation, the concentration of water in the liquid reaction composition in the first reaction zone is preferably in the range 0 to 15% by weight.

Preferably, the concentration of methyl iodide co-catalyst in the liquid carbonylation reaction compositions in the first and optional further reaction zones is independently in the range from 2 to 20% by weight, preferably from 4 to 18% by weight.

Carbon monoxide is suitably present in the first reaction zone at a partial pressure of from 0 to 40 bar (0 to 4 MPa), preferably 4 to 30 bar (0.4 to 3 MPa). The carbon monoxide reactant for the carbonylation reactions may be essentially pure or may contain inert impurities such as carbon dioxide, methane, nitrogen, noble gases, water and $C_1$ to $C_4$ paraffinic hydrocarbons. The presence of hydrogen in the carton monoxide and generated in situ by the water gas shift reaction is preferably kept low as its presence may result in the formation of hydrogenation products. Thus, the amount of hydrogen in the carbon monoxide reactant is preferably less than 1 mol %, more preferably less than 0.5 mol % and yet more preferably less than 0.3 mol % and/or the partial pressure of hydrogen in the reaction zone is preferably less than 1 bar (0.1 MPa) partial pressure, more preferably less than 0.5 bar (50 kPa) and yet more preferably less than 0.3 bar (30 kPa).

Acetic acid product is recovered from the first and optional further reaction zones by flash separation. In flash separation liquid reaction composition is passed to one or more flash separation stages via a flashing valve. A flash separation stage may be an adiabatic flash vessel or may have additional heating means. In the flash separation stage the liquid fraction, which comprises the majority of the carbonylation catalyst and the majority of the carbonylation promoter metal is separated from the vapour fraction, which comprises acetic acid, methyl acetate, water, methyl iodide and non-condensable gases such as nitrogen, carbon monoxide, hydrogen and carbon dioxide. The liquid fraction is recycled to the first reaction zone and the vapour fraction may be passed to one or more distillation zones. In a first distillation zone acetic acid product is separated from the light components (methyl iodide and methyl acetate). The light components are removed overhead, and recycled to the first and/or optional further reaction zones. Also removed overhead is a low pressure off-gas comprising the non-condensable gases such as nitrogen, carbon monoxide, hydrogen and carbon dioxide. Such a low-pressure off-gas stream may be passed through an off-gas treatment section to remove condensable materials such as methyl iodide, prior to being vented to atmosphere, for example, via a flare.

The acetic acid produced by the process according to the present invention may be further purified by conventional processes, for example further distillation to remove impurities such as water, unreacted carbonylation reactant and/or ester derivative thereof and higher-boiling by-products.

The process of the present invention may performed as a continuous process, wherein determination of the concentration of the first catalytic species or of the ratio of the concentrations of the first and second catalytic species takes place at appropriate intervals such that maintenance of the concentration of the first catalytic species or of the ratio of the concentrations of the first and second catalytic species is substantially constant.

BRIEF DESCRIPTION OF THE DRAWINGS

The invention will now be illustrated by the following non-limiting examples and with reference to FIG. 1, which represents a schematic form of apparatus suitable for carrying out the process of the present invention.

DETAILED DESCRIPTION OF PREFERRED EMBODIMENTS

The apparatus comprises a first reaction zone (3), a second reaction zone (5), and a flash separation stage (6). In use, methanol and carbon monoxide are fed to the first reaction zone (3) via lines (1) and (2) respectively. In the first reaction zone (3) carbon monoxide is contacted with a liquid reaction composition which comprises iridium catalyst and ruthenium catalyst promoter metal, methanol, methyl acetate, water, methyl iodide and acetic acid. Liquid reaction composition is withdrawn from the first reaction zone (3) via line (4), and is passed through a second reaction zone (5), in which the carbon monoxide dissolved and/or entrained in the liquid reaction composition reacts further to produce additional acetic acid. The liquid reaction composition is then fed to flash separation stage (6), wherein it is separated into two phases: a vapour fraction and a liquid fraction. The vapour fraction comprising acetic acid, methyl iodide, water, methanol and methyl acetate, is fed via line (7) to a distillation zone (not shown) for recovery of purified acetic acid. The liquid fraction, comprising iridium and ruthenium catalytic species and acetic acid, is returned to the first reaction zone (3) via line (8).

In the following examples acetic acid was produced by the iridium catalysed, ruthenium promoted carbonylation of methanol, using the apparatus represented in FIG. 1.

In the liquid reaction composition in the first reaction zone there existed a first soluble catalytic species, $[Ru(CO)_2I_2]_n$, and a second soluble catalyst species, $[Ru(CO)_3I_3]^-$, in equilibrium therewith. In the examples below the ratio of the concentration of $[Ru(CO)_2I_2]_n$ to the concentration $[Ru(CO)_3I_3]^-$ present in the liquid fraction from the flash separation stage which was recycled to the first reaction zone (8) was determined and the predetermined value below which the ratio was to be maintained was the value at which ruthenium precipitates occur.

General Method for Determining the Ratio of Concentrations

An infrared spectrometer (Applied Systems ReactIR, model 001-1003) was calibrated by reference to a series of solutions comprising known concentrations of $[Ru(CO)_2I_2]_n$ and $[Ru(CO)_3I_3]^-$. The calibration was based on suitable infrared absorption bands corresponding to $[Ru(CO)_2I_2]_n$ and $[Ru(CO)_3I_3]^-$ respectively.

Off-line infrared measurements were made on samples taken from the liquid fraction which is recycled to the first reaction zone (8) and the ratio of the concentration of $[Ru(CO)_2I_2]_n$ to the concentration $[Ru(CO)_3I_3]^-$ present in the liquid fraction recycled to the first reaction zone (8) was determined.

Example A

The carbonylation process was operated at a carbon monoxide concentration in the vapour fraction of the flash stage of 20% by volume. The concentration of $[Ru(CO)_2I_2]_n$ in the liquid fraction was 3100 ppm, and the concentration of $[Ru(CO)_3I_3]^-$ was 310 ppm, in which the ppm values relate to the quantity of elemental ruthenium. Thus, the ratio of the concentration of $[Ru(CO)_2I_2]_n$ to the concentration $[Ru(CO)_3I_3]^-$ present in the liquid fraction was 10.

In this example the formation of a ruthenium-containing precipitate in the liquid fraction was observed. Thus, the predetermined value below which the ratio of the concentration of $[Ru(CO)_2I_2]_n$ to the concentration $[Ru(CO)_3I_3]^-$ had to be maintained was 10.

Example 1

The feed rate of carbon monoxide to the second reaction zone in the process of Example A was adjusted such that the process was operated at a carbon monoxide concentration in the vapour fraction of the flash stage of 40% by volume. The concentration of $[Ru(CO)_2I_2]_n$ in the liquid fraction was 3365 ppm, and the concentration of $[Ru(CO)_3I_3]^-$ was 370 ppm, in which the ppm values relate to the quantity of elemental ruthenium. Thus, the ratio of the concentration of $[Ru(CO)_2I_2]_n$ to the concentration $[Ru(CO)_3I_3]^-$ present in the liquid fraction was 9.1. No precipitation was observed in the liquid fraction. This is an example according to the present invention, since the concentration of $[Ru(CO)_2I_2]_n$ was adjusted (indirectly by adjustment of carbon monoxide feed rate) such that the ratio of the concentration of $[Ru(CO)_2I_2]_n$ to the concentration $[Ru(CO)_3I_3]^-$ present in the liquid fraction was maintained below the value at which ruthenium precipitates occur.

Example 2

The feed rate of carbon monoxide to the second reaction zone in the process of Example A was adjusted such that the process was operated at a carbon monoxide concentration in the vapour fraction of the flash stage of 40% by volume, and lithium iodide was introduced into the process to give a concentration thereof in the reaction zone of 35 ppm. The concentration of $[Ru(CO)_2I_2]_n$ in the liquid fraction was 3910 ppm, and the concentration of $[Ru(CO)_3I_3]^-$ was 670 ppm, in which the ppm values relate to the quantity of elemental ruthenium. Thus, the ratio of the concentration of $[Ru(CO)_2I_2]_n$ to the concentration $[Ru(CO)_3I_3]^-$ present in the liquid fraction was 5.8. No precipitation was observed in the liquid fraction. This is an example according to the present invention, since the concentration of $[Ru(CO)_2I_2]_n$ was adjusted (indirectly by adjustment of carbon monoxide feed rate and by addition of lithium iodide) such that the ratio of the concentration of $[Ru(CO)_2I_2]_n$ to the concentration $[Ru(CO)_3I_3]^-$ present in the liquid fraction was maintained below the value at which ruthenium precipitates occur.

TABLE 1

| Example | Concentration of $[Ru(CO)_2I_2]_n$ | Concentration of $[Ru(CO)_3I_3]^-$ | $[Ru(CO)_2I_2]_n$/$[Ru(CO)_3I_3]^-$ Ratio | Precipitate |
| --- | --- | --- | --- | --- |
| A | 3100 | 310 | 10 | Yes |
| 1 | 3365 | 370 | 9.1 | No |
| 2 | 3910 | 670 | 5.8 | No |

These results show that an iridium-catalysed, ruthenium-promoted methanol carbonylation process can be optimised by determining the ratio of the concentration of a first soluble catalytic species to a second soluble catalytic species in equilibrium therewith in the liquid fraction from the flash separation stage, and adjusting the concentration of the first species such that the ratio of concentrations is maintained below a predetermined value. The process is optimised by avoiding the formation of ruthenium precipitates.

Further, comparison of Example 1 and Example 2 demonstrates that the concentration of the first species need only be adjusted to the extent that is necessary to maintain the ratio of concentrations below a predetermined value, and can thereby avoid wasting resources. In particular, Examples 1 and 2 demonstrate that it is unnecessary to add lithium iodide in addition to increasing the carbon monoxide concentration in the vapour fraction of the flash stage in order to maintain the ratio below the value at which ruthenium precipitates occur.

The invention claimed is:

1. A process for the production of acetic acid which process comprises the steps of:
   (a) carbonylating methanol and/or a reactive derivative thereof with carbon monoxide in a first reaction zone containing a liquid reaction composition comprising an iridium carbonylation catalyst and a carbonylation catalyst promoter metal, methyl iodide, methyl acetate, acetic acid and optionally water, and in which liquid reaction composition there exists in equilibrium at least a first soluble promoter metal catalytic species and a second soluble promoter metal catalytic species, wherein the first promoter metal catalytic species is the least catalytically active or promotionally active of the species existing in the equilibrium;
(b) withdrawing liquid reaction composition together with dissolved and/or entrained carbon monoxide and other gases from said first reaction zone;
(c) optionally passing said withdrawn liquid reaction composition through one or more further reaction zones to consume at least a portion of the dissolved and/or entrained carbon monoxide;
(d) passing said liquid reaction composition from step (b) and optional step (c) into one or more flash separation stages to form a vapour fraction, which comprises condensable components and low-pressure off-gas, the condensable components comprising acetic acid product, methyl iodide, methyl acetate and optional water, and the low-pressure off-gas comprising carbon monoxide and other gases dissolved and/or entrained in the withdrawn liquid reaction composition, and a liquid fraction, which comprises carbonylation catalyst, carbonylation catalyst promoter metal and acetic acid solvent; and
(e) recycling the liquid fraction from the flash separation stage to the first reaction zone;
(f) determining (i) the concentration of the first promoter metal catalytic species and/or (ii) the ratio of the concentration of the first promoter metal catalytic species to the concentration of the second promoter metal catalytic species in equilibrium therewith, present in the liquid reaction composition in any of steps (a) to (d), and/or present in the liquid fraction in step (e); and
(g) maintaining (i) and/or (ii) below a pre-determined value.

2. A process as claimed in claim 1, in which the ratio of the concentration of the first promoter metal catalytic species to the concentration of the second promoter metal catalytic species present in the liquid reaction composition in any of steps (a) to (d), and/or present in the liquid fraction in step (e) is determined and maintained below a pre-determined value.

3. A process as claimed in claim 1, in which the concentration or ratio of concentrations is determined by infrared spectroscopy.

4. A process as claimed in claim 3 in which the infrared spectroscopy is carried out on-line.

5. A process as claimed in claim 3 in which the infrared spectroscopy is carried out off-line.

6. A process as claimed in claim 3, in which infrared frequencies in the range of from 2500 to 1500 $cm^{-1}$ are used.

7. A process as claimed in claim 1, in which the catalyst promoter metal is selected from the group consisting of ruthenium, osmium, rhenium, cadmium, mercury, zinc, gallium, indium, tungsten and mixtures thereof.

8. A process as claimed in claim 7, in which the promoter metal is ruthenium.

9. A process as claimed claim 1, in which (i) or (ii) present in the liquid fraction in step (e) is determined and maintained below a predetermined value.

10. A process as claimed in claim 1, wherein (i) and/or (ii) are maintained below a pre-determined value in step (g) by adjusting the concentration of at least the first promoter metal catalytic species present in the liquid reaction composition in any of steps (a) to (d), and/or present in the liquid fraction in step (e).

* * * * *